United States Patent [19]

Turcotte

[11] 4,288,540

[45] Sep. 8, 1981

[54] REAGENT FOR THE EARLY DETECTION OF CANCER

[76] Inventor: Hector Turcotte, 1572 du Ruisseau Ave., Sillery, Quebec, Canada, G1S 3V1

[21] Appl. No.: 148,257

[22] Filed: May 9, 1980

[51] Int. Cl.³ ............................................. G01N 33/54
[52] U.S. Cl. ........................................ 435/7; 435/176; 435/177; 435/180; 424/12
[58] Field of Search ............... 424/12; 435/7, 29, 176, 435/177, 180; 23/230 B

[56] References Cited

U.S. PATENT DOCUMENTS 3,669,841 6/1972 Miller .................................. 435/176
3,953,292 4/1976 Burns .................................. 435/176
4,078,971 3/1978 Arkles et al. ........................ 435/180

OTHER PUBLICATIONS

AKSAC, S., "Antibody Formation against Agrobacterium tumefaciens in Patients with Various Cancers"; Turk Hij. Tecr. Biyol., Derg. 34 (1-2) pp. 48-51 (1974).

Lippincott, B. B. et al., "Plasmid Content and Tumor Initiation Complementation by Agrobacterium tumefaciens IIBNV6", Jour. of Bact., vol. 132, pp. 824-831 (1977).

Farrand, S. K. et al., Biochemica et Biophysica Acta, 390, pp. 264-275, (1975).

*Primary Examiner*—Benoit Castel
*Attorney, Agent, or Firm*—Robic, Robic & Associates

[57] ABSTRACT

A reagent for the early detection of cancer. The reagent is employed in a method comprising the steps of contacting the reagent which consists of bacillus agrobacterium tumefaciens adsorbed on red blood cells, yeast cells or particles selected from the group consisting of polyvinyl latex, kaolin and animal black, with a patient's blood serum and determining whether there a positive reaction of agglutination. The presence of such a reaction indicates that the patient has a cancer in evolution.

7 Claims, No Drawings

REAGENT FOR THE EARLY DETECTION OF CANCER

The present invention relates to a reagent for the early detection of cancer by immunologic agglutination of bacillus agrobacterium tumefaciens.

For more than one hundred years, the only method for detecting cancer in humans has been to remove surgically a little portion of the tumor and to examine it with a microscope to look for cancer cells in the tissue. Unfortunately this surgical intervention can only be carried out when the tumor has attained a certain volume or begins to be the cause of functionnal disorders. As this method can be used only when clinical symptoms are present, it cannot be considered as the best one for an early diagnosis of cancer or, in other words, it cannot be used as a screening test routinely made before any clinical sign of cancer.

For many years, the present inventor was convinced that, when cancer cells are developing in the human body, they create a state of defense producing humoral antibodies against cancer. Therefore, it should be possible to detect the presence of those antibodies (anticancer) by using an antigen causing the cancer. However, as no agent causing the cancer in humans is presently known, he thought that the agent causing the cancer on some plants could be used for this purpose. This agent is a microorganism known as "bacillus agrobacterium tumefaciens". With confidence, he used it as antigen and fortunately obtained a positive agglutination of the bacillus when mixed with the serum of a cancerous patient.

Accordingly, the purpose of the present invention is to provide a reagent employed in a method for the early detection of cancer comprising the steps of contacting a reagent containing bacilli agrobacterium tumefaciens with a patient's serum and determining whether there is a positive reaction of agglutination, the presence of such a reaction indicating that the patient has a cancer in evolution. In accordance with the invention, the reagent consist of bacillus agrobacterium tumefaciens adsorbed on red blood cells, on yeast cells or on particles selected from the group consisting of polyvinyl latex, kaolin and animal black. When the bacilli agrobacterium tumefaciens adsorbed on the red blood or yeast cells or inorganic particles are mixed with the serum of a cancerous person, the antibodies present in the serum react with this antigen and a positive reaction of agglutination of the red blood (haemagglutination or yeast cells or of the inorganic particles can be observed.

The invention and its advantages will be better understood with reference to the following description of several specific examples.

EXAMPLE 1

A reagent for the early detection of cancer was prepared, using human red blood cells group O, Rh negative as support for the bacillus agrobacterium tumefaciens. The human red blood cells were washed three (3) times with a 0.85% solution of NaCl and mixed with a suspension of bacilli agrobacterium tumefaciens preheated during 1 hour in a 100° C. water bath.

The suspension was prepared as follows: the bacillus agrobacterium tumefaciens, strain 17022 from the Department of Agriculture of Canada, was inoculated on the surface of a slanted Sabouraud glucose agar and placed into an incubator at 25° C. for a period of seven to ten days. After this time of incubation, the microbes were washed off from the surface of the agar with a solution of NaCl in sufficient quantity to bring the suspension to a density corresponding to the No 7 or 8 of the McFarland scale. Thereafter, the suspension was heated for one (1) hour in a boiling water bath to liberate the soluble extract of the bacillus.

To wash and mix the red blood cells with the bacillus agrobacterium tumefacien, the following procedure was used. Into a conical screw cap centrifuge tube, 0.1 ml of packed erythrocytes (red blood cells) previously washed three (3) times, 0.1 ml of the extract of the bacillus and 0.5 ml of the solution of NaCl were inserted. The mixture was mixed and placed into a 37° C. water bath for 30 minutes. Then the red cells were washed three (3) times with a solution of NaCl and finally resuspended into 4.0 ml of a solution of NaCl before being stored in an ice-box at a temperature of 3° to 8° C. The so obtained reagent could stay unhaemolised for one week but it could even stay for a longer period of time provided that use is made of red blood cells treated with formalin.

EXAMPLE 2

A reagent for the early detection of cancer was prepared by using a suspension of yeast cells (Fleisham $^R$) instead of human red blood cells as disclosed in example 1. This substitution changed nothing in the way of carrying out the detection test or in the result of the reaction, except that the reaction seemed to occur more rapidly. The sole difference laid in that the agglutinated yeast cells formed white aggregates instead of red ones.

In this regard, it should be noted that the use of yeast cells facilitates the preparation of the reagent because it is not necessary to wash the cells as it is when red blood cells are used. Also, the preservation of the reagent is indefinite because there is no haemolysis of the cells.

To prepare the reagent, the following procedure was used. Into a screw cap test tube, 0.3 ml of chromium chloride, 0.1% in a solution of NaCl, 0.3 ml of soluble extract of the bacillus and finally 2.0 ml of a suspension of yeast cells in a solution of NaCl were introduced in this order. The density of the obtained suspension corresponded to No 4 in the scale of McFarland. The mixture was placed into a 37° C. water bath for a period of 30 minutes and subsequently for one night in the icebox 3° to 8° C.

EXAMPLE 3

Using substantially the same procedure as in example 2, a reagent was prepared by using a suspension of kaolin instead of yeast cells. This substitution changed nothing in the way of carrying out the detection test nor in the result of the reaction.

EXAMPLE 4

Using substantially the same procedure as in example 2, a reagent was prepared by using a suspension of animal black instead of yeast cells. This substitution changed nothing in the way of carrying out and reading the detection test except that the formed aggragates were black.

EXAMPLE 5

Using substantially the same procedure as in example 2, a reagent was prepared by using a suspension of spherules of polyvinyl latex having a diameter of 0.81μ (BACTO-LATEX 0.81 code 3102 produced by DIFCO LAB. of Detroit, Michigan). This substitution changed nothing in the way of carrying out and reading the detection test.

EXAMPLE 6

Test made on a glass slide

Into one circle on a glass slide were placed 40 $\mu$l of blood serum of a cancerous patient, diluted in a solution of NaCl (1 part of serum per 2 parts of saline). 2 drops of the sensitized erythrocytes obtained in example 1 were added directly into the serum using a Kline pipette, and were well mixed with a toothpick following a circling motion to spread the mixture and form a spot having a diameter of about one centimeter. The slide was held with both hands and shaked with a simultaneous rocking and rotation motion for 2 or 3 minutes. The rocking and rotation motion was carried out very slowly over a concave mirror and under the light of a fluorescent lamp, to aid the observer to appreciate the agglutination.

The agglutination progressed this way. The mixture of serum-red cells first formed a cloudy red liquid which clarified gradually. In the meantime, there was formation of aggregates or deep red grains coalescing in the center of the reaction circle. It was necessary to look into the mirror and not on the slide to appreciate the agglutination.

Usually, a "direct reaction" will occur within two or three minutes. If the reaction is doubtfull, the slide must be placed into a petri dish on a wet gauze till the next morning. If the reaction is negative, the mixture will stay cloudy and, while the slide is rotated, the red cells will concentrate in a button-like pattern in the center of the mixture.

EXAMPLE 7

Test made into a test tube

Into a round bottom test tube of 75×9 mm, were placed 2.0 ml of a solution of NaCl and 2 drops of an undiluted cancerous patient's serum with a Pasteur pipette. The solution was well mixed by inversion of the tube and 2 drops of the complex of agrobacterium tumefaciens bacillus and red blood cells obtained in example 1 was added with a kline pipette. The mixture was mixed again by inversion of the tube. The tube was finally placed vertically on a test tube rack for 12 or 24 hours before the lecture of the reaction. The rack was placed on a vibrationless table. After 24 hours, the red cells were agglutinated and settled to the bottom of the test-tube as a diffuse carpet, such proving a positive reaction.

In a negative reaction, the red cells will appear as a small circle or compact red button at the bottom of the test tube.

It should be noted that false positive reaction will be obtained with the serum of a pregnant woman of a woman using anovulatory pills. It should also be noted that false negative reaction will also be observed with the serum of cancerous patient on chemotherapy.

What is claimed is:

1. A reagent for the early detection of cancer, comprising the water soluble extract of bacillus agrobacterium tumefaciens, strain 17022, adsorbed on red blood cells, on yeast cells or on particles selected from the group consisting of polyvinyl latex, kaolin and animal black.

2. A reagent as claimed in claim 1, wherein the water soluble extract of bacillus agrobacterium tumefaciens is adsorbed on red blood cells, group O, Rh negative.

3. A reagent as claimed in claim 1, wherein the water soluble extract of bacillus agrobacterium tumefaciens is adsorbed on yeast cells.

4. A reagent as claimed in claim 1, wherein the water soluble extract of bacillus agrobacterium tumefaciens is adsorbed on spherules of polyvinyl latex.

5. A reagent as claimed in claim 4, wherein the spherules have a diameter of about 0.81$\mu$.

6. A reagent as claimed in claim 1, wherein the water soluble extract of bacillus agrobacterium tumefaciens is adsorbed on kaolin.

7. A reagent as claimed in claim 1, wherein the water soluble extract of bacillus agrobacterium tumefaciens is adsorbed on animal black.

* * * * *